United States Patent [19]

Akhavi

[11] 4,240,426
[45] Dec. 23, 1980

[54] SYRINGE COUPLING SYSTEM

[75] Inventor: David S. Akhavi, Los Angeles, Calif.

[73] Assignee: American Hospital Supply Corporation, Evanston, Ill.

[21] Appl. No.: 953,609

[22] Filed: Oct. 23, 1978

[51] Int. Cl.³ .............................................. A61M 5/00
[52] U.S. Cl. ................................. 128/218 N; 128/221
[58] Field of Search ........... 128/128 R, 128 N, 128 S, 128/215, 216, 221

[56] References Cited

U.S. PATENT DOCUMENTS

| Re. 28,713 | 2/1976 | Stevens et al. | 128/221 |
|---|---|---|---|
| 2,844,149 | 7/1958 | Gettig | 128/221 |
| 3,179,107 | 4/1965 | Clark | 128/221 |
| 3,301,256 | 1/1967 | Cowley | 128/218 |
| 3,381,813 | 5/1968 | Coanda et al. | 128/218 S |
| 3,472,227 | 10/1969 | Burke | 128/221 |
| 4,040,421 | 8/1977 | Young | 128/218 N |
| 4,058,121 | 11/1977 | Choksi et al. | 128/221 |

OTHER PUBLICATIONS

Chemical Engineer's Handbook, Fifth Edition, R. Perry 1973.

Primary Examiner—John D. Yasko
Attorney, Agent, or Firm—Larry N. Barger

[57] ABSTRACT

A hypodermic needle having a hub of polycarbonate which is extremely adherent to an epoxy for securing a cannula to the hub. A syringe barrel adapter of a material softer than polycarbonate; i.e., polypropylene, is wedge fitted to the hub and compressively cold flows slightly during storage to prevent long term crazing or stress cracking of the polycarbonate hub.

2 Claims, 3 Drawing Figures

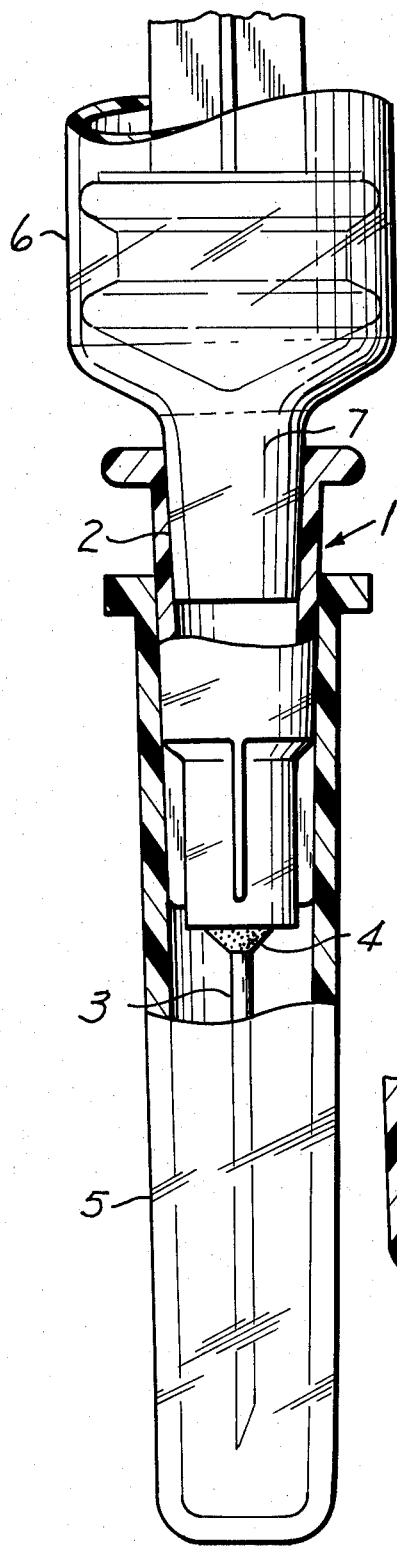
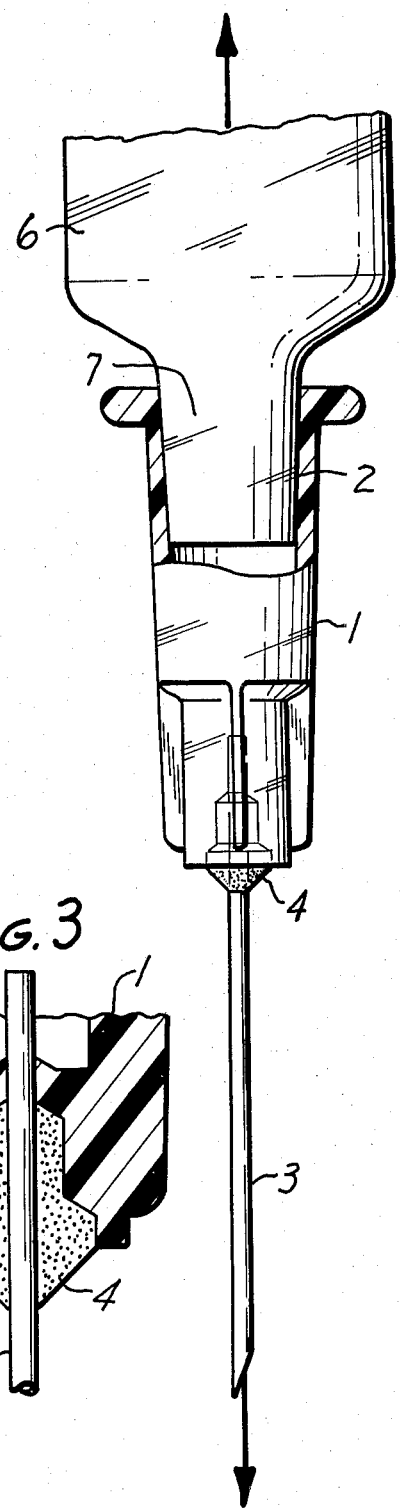
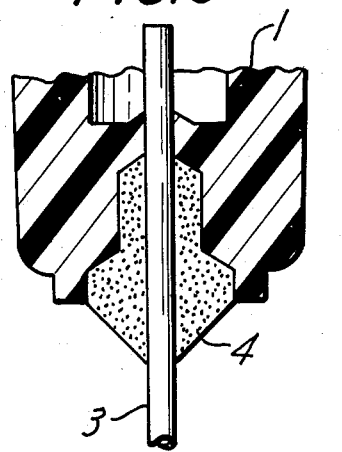

SYRINGE COUPLING SYSTEM

BACKGROUND

One of the major problems in hypodermic syringe construction is the needle hub which forms a connecting unit between a hypodermic syringe barrel and a puncturing cannula. Numerous types of hub designs have been proposed to provide reliable and very firm connection between the cannula and the needle hub. The hub must also provide a very reliable seal with the syringe barrel's tapered adapter. Different materials have been used in the past for needle hubs. Polypropylene has been used for hubs, but has very little adherence to epoxies or other adhesives used to join the hub and cannula. Because of this shortcoming of polypropylene, various attempts have been made to mechanically anchor the epoxy to the hub. Epoxy will bond readily to the metal cannula, but not to the polypropylene hub. Difficult to mold undercut pockets have been proposed in U.S. Pat. No. 3,179,107, as well as expensive separate holding sleeves as in U.S. Pat. No. 3,472,227. Various other types of crimped anchoring structure such as in U.S. Pat. No. Re. 28,713 and 2,844,149 have been proposed for securing a metal cannula to a thermoplasitc needle hub.

Nylon has also been used in hubs because it has very good adherent properties to epoxy. No expensive undercut structure was required in the nylon hub. However, nylon tends to readily absorb moisture when subjected to elevated temperatures or humid environments and such absorbed moisture tends to slightly alter the hub's dimensional configuration, sometimes causing the hub to become loosened on the tapered adapter of the syringe barrel during long storage periods.

SUMMARY OF THE INVENTION

The problems of polypropylene and nylon hubs explained above have been overcome by the present invention which has unexpectedly found that a polycarbonate needle hub can form a very secure fit over long periods of time with a syringe barrel's tapered adapter of a material substantially softer than the polycarbonate without crazing or stess cracking the polycarbonate hub. This is because the softer barrel adatper cold flows very slightly under compressive forces to prevent long term crazing or stress cracking of the polycarbonate hub which is under hoop stress. The polycarbonate hub is extremely adherent to epoxy for anchoring the cannula to the hub.

A related application entitled "Syringe With Plug Type Needle Hub Lock," Ser. No. 953,608, filed Oct. 23, 1978, has a sealing portion of a hub under compression hoop stresses, and is very well suited for small size insulin syringes of 1cc size or smaller.

THE DRAWINGS

FIG. 1 is a sectional view of a protector encased needle assembled to a syringe barrel;

FIG. 2 is a sectional view illustrating separational pull forces used to test the holding power between the hub and syringe; and FIG. 3 is an enlarged view of the epoxy pocket in the hub.

DETAILED DESCRIPTION

FIG. 1 shows a needle hub 1 of polycarbonate having an internal tapered section 2 that can be in the form of a standard Luer taper. A cannula 3 is secured to a forward end of the hub by an adhesive, such as an epoxy, 4. No undercuts are needed in the hub as shown in the enlarged view of FIG. 3. During pull tests, it was unexpectedly found that the epoxy to the polycarbonate and cannula bond was so good that it took approximately 30 lbs. of force to separate the cannula and hub. This is well in excess of what is normally considered safe. A protector 5 is removably mounted on hub 1.

A syringe barrel 6 has externally tapered adapter 7 of a material softer than polycarbonate. It has been unexpectedly found that such interconnecting relationships between these two materials solves a crazing or stress cracking problem that is well-known to exist with polycarbonate materials. When a very hard polycarbonate material is under stress for extended periods of time, the material develops small surface cracks known as crazing. If the cracks proceed completely through the part, they are known as stress cracks. Such crazing or stress cracking is believed to be due to the cyrstalline structure of polycarbonate.

Crazing or stress cracking of a polycarbonate hub would not normally be a problem with hubs that are sold separately from the syringe barrel and assembled immediatedly prior to injection. Crazing and stress cracking occur over long periods of time, such as several days or months. Many of the hypodermic syringes sold today are sold with a preconnected needle, and since such hub is under continual stress during warehouse storage, shipments, etc., it would be expected that crazing and stress cracking would render a polycarbonate hub unsuitable.

The applicants have unexpectedly found that the soft polypropylene adapter of the syringe barrel overcomes such crazing and stress cracking problems which still occur with the polycarbonate hub stored for long periods of time on a *glass* adapter which does not cold flow with extended compressive forces.

Comparative tests were made between nylon, polypropylene, and polycarbonate relative to the force necessary to separate a syringe barrel from a needle after such needle is applied with a staking force of 20 lbs. It was shown that the polycarbonate hub was substantially better than the other two. The results of pull forces both before and after autoclaving are summarized below.

|  | Befoe Autoclaving | After Autoclaving |
| --- | --- | --- |
| Nylon | 5 lbs. | 2 lbs. |
| Polypropylene | 8 lbs. | 3 lbs. |
| Polycarbonate | 9 lbs. | 4 lbs. |

While the above tests were made with syringes not having a threaded collar in addition to the tapered adapter, such as shown in U.S. Pat. No. 3,301,256, the higher retention forces of polycarbonate would have advantages for such collared syringe because such high retention forces would prevent inadvertent unscrewing removal of the hub from the collared syringe.

The applicants have also found that it is important during the manufacturing procedure of the syringe barrel and needle hub to attach the hub to the syringe barrel adapter prior to any substantial compressive forces being applied to the adapter. Thus, to avoid any crazing and stress cracking problems, the polycarbonate hub should make the virgin connection to the syringe. It has been noted that syringes that have been stored for a considerable time with one polycarbonate hub will not perform the crazing protection to a substitute polycarbonate hub fitted to such syringe. This is believed to be due to substantially all of the cold flow having occurred in the barrel adapter and there was substantially no cold flow left to protect the second polycarbonate hub. Thus, a previously stored polypropylene syringe barrel acts somewhat like a glass barrel when attached to the polycarbonate hub.

In the foregoing description, a specific example has been used to describe the invention. It is understood by those skilled in the art that certain modifications can be made to this example without departing from the spirit and scope of the invention.

I claim:

1. A syringe coupling system comprising: a cylindrical metal cannula; a polycarbonate needle hub with a longitudinal axis; which hub has a hollow forwardly opening pocket at its forward end, the pocket having an inner surface that is spaced from the metal cannula by a distance that is approximately constant or increases in a forward direction along the length of the pocket without any substantial transverse groove or undercut recess into the pocket's inner surface; an epoxy in the pocket bonding the metal cannula to the polycarbonate inner wall of the pocket with the metal-epoxy-polycarbonate joint capable of withstanding a longitudinal separation force of approximately 30 lbs. or more without the cannula pulling out of the hub; said hub having a hollow internally tapered section at its rear end; and a syringe barrel with an externally tapered adapter of a thermoplastic softer than polycarbonate wedgingly fitted into the hub's internal tapered section with the adapter being free of substantial external compression forces prior its assembly to the hub, whereby the hub will reliably stay on the adapter until intentionally removed and the hub will securely support the cannula.

2. A method of forming a syringe for long storage comprising:
   (a) forming a needle hub of polycarbonate with a longitudinal axis, said hub having at its forward end a hollow forwardly opening pocket with an inner surface that is approximately parallel to the hub's longitudinal axis or diverges in a forward direction along the hub providing a pocket without any substantial transverse groove or undercut recess into the pocket's inner surface, and the hub has at its rear end a hollow internally tapered section;
   (b) forming a syringe barrel with an externally tapered adapter of a material softer than polycarbonate;
   (c) securing a cylindrical metal cannula in the hub's pocket by means of an epoxy so the metal-epoxy-polycarbonate joint is capable of withstanding a longitudinal separation force of approximately 30 lbs. or more without the cannula pulling out of the hub; and
   (d) wedging the hub onto the barrel adapter prior to any other substantial external compression forces being applied to the barrel adapter, whereby the barrel adapter can cold flow slightly during long storage periods to prevent long term stresses reaching a level that would cause crazing of the polycarbonate hub.

* * * * *